United States Patent
Rortais et al.

(10) Patent No.: US 8,481,589 B2
(45) Date of Patent: Jul. 9, 2013

(54) TAXOID-BASED COMPOSITIONS

(75) Inventors: Patricia Rortais, Paris (FR); Carine Gachon, Paris (FR)

(73) Assignee: Aventis Pharma S.A., Antony (FR)

( * ) Notice: Subject to any disclaimer, the term of this patent is extended or adjusted under 35 U.S.C. 154(b) by 488 days.

(21) Appl. No.: 12/757,255

(22) Filed: Apr. 9, 2010

(65) Prior Publication Data

US 2010/0311825 A1 Dec. 9, 2010

Related U.S. Application Data

(63) Continuation of application No. PCT/FR2008/001410, filed on Oct. 9, 2008.

(30) Foreign Application Priority Data

Oct. 10, 2007 (FR) ..................... 07 07092

(51) Int. Cl.
- *A01N 43/02* (2006.01)
- *A61K 31/335* (2006.01)
- *C07D 305/00* (2006.01)
- *C07D 407/00* (2006.01)
- *C07D 493/00* (2006.01)

(52) U.S. Cl.
USPC .......................... 514/449; 549/510

(58) Field of Classification Search
USPC .......................... 514/449; 549/510
See application file for complete search history.

(56) References Cited

U.S. PATENT DOCUMENTS

| | | | | |
|---|---|---|---|---|
| 5,254,580 | A | * | 10/1993 | Chen et al. ............... 514/449 |
| 5,403,858 | A | | 4/1995 | Bastart et al. |
| 5,415,869 | A | * | 5/1995 | Straubinger et al. ......... 424/450 |
| 5,438,072 | A | | 8/1995 | Bobee et al. |
| 5,616,330 | A | * | 4/1997 | Kaufman et al. ............ 424/400 |
| 5,750,561 | A | | 5/1998 | Bastart et al. |
| 6,537,579 | B1 | | 3/2003 | Desai et al. |
| 2002/0001613 | A1 | * | 1/2002 | Niemiec et al. .............. 424/450 |
| 2003/0099674 | A1 | | 5/2003 | Chen |

FOREIGN PATENT DOCUMENTS

| | | | |
|---|---|---|---|
| EP | 0 593 601 | B1 | 4/1994 |
| EP | 0 593 656 | B1 | 4/1994 |
| EP | 0 671 912 | B1 | 9/1995 |

OTHER PUBLICATIONS

Strickley, Pharmaceutical Research, 2004, Plenum Publishing Corp., vol. 21, No. 2, pp. 201-230.*
Rawinsky et al, Taxol: A Novel Investigational Antimicrotubule Agent, J. of National Cancer Institute, 1990 (82)15 pp. 12447-1259.
International Search Report for WO2009/083664 dated Jul. 9, 2009.

* cited by examiner

*Primary Examiner* — Sreeni Padmanabhan
*Assistant Examiner* — Sarah Pihonak
(74) *Attorney, Agent, or Firm* — Hamilton, Brook, Smith & Reynolds, P.C.

(57) ABSTRACT

The disclosure relates to novel taxoid-based compositions comprising injectable formulations of these derivatives in the form of an emulsion.

20 Claims, No Drawings

TAXOID-BASED COMPOSITIONS

The present invention relates to a novel pharmaceutical form based on a therapeutic agent that has antitumour and antileukemic activity. It relates more particularly to a novel injectable form containing the derivative of general formula (I) below:

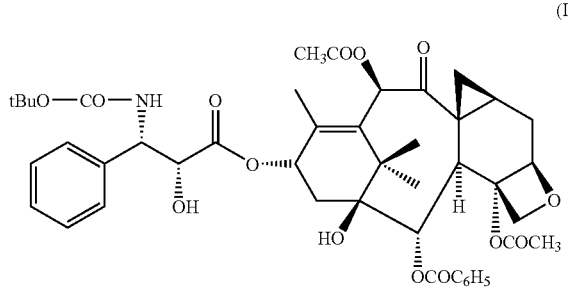

or the derivative of general formula (II) below:

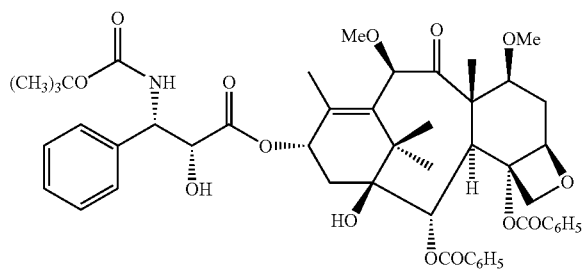

The compound of formula (I) is better known under the international non-proprietary name larotaxel, it is currently in clinical trials and known by the abbreviation XRP9881. The compound of formula (II) is also currently in clinical trials and known by the name XRP6258.

These products exhibit, in vivo, a substantial activity on malignant tumours that has enabled them to be studied in the treatment of diseases that are resistant to all other anti-cancer therapies.

Unfortunately, this type of product, especially docetaxel or paclitaxel, has such a low solubility in water that it has been necessary to prepare a formulation for an injectable preparation based on a surfactant and ethanol. Ethanol is the best pharmaceutical solvent that makes it possible to dissolve the molecules corresponding to formula (I) and to formula (II). Such a formulation is, for example, described in Patent EP 0 593 656 or in the following publication.

By way of example, according to the publication by Rowinsky, Lorraine, Cazenave and Donehower which appeared in the Journal of the National Cancer Institute, Vol. 82, No. 15, pages 1247-1259 on 1 Aug. 1990, concerning Taxol which has a solubility close to the compounds of formula (I) or (II) a first solution, known as a "stock solution", is prepared that contains approximately 6 mg/ml of taxol in a solvent mixture composed of:
    50 vol % ethanol; and
    50 vol % polyoxyethylenated castor oil (e.g. Cremophor EL).

Still according to this publication, in order to obtain such concentrations (between 0.3 and 1 mg/ml), it is necessary to inject solutions containing, at the same time as the active principle, concentrations of each of the following compounds, ethanol and above all Cremophor, of approximately 8 g per 100 of perfusion solution. Since the treatment often requires the administration of high doses of active principle, and since the concentration of the active principle in the solution is relatively low, the injection of a large volume has the effect of causing, in addition to anaphylactic manifestations, manifestations of alcohol poisoning during the treatment.

It has been discovered, according to European Patent EP 0 593 601, that the use of different pharmaceutical forms made it possible either to greatly reduce the ethanol concentrations, or else to completely remove the Cremophor and the ethanol in perfusion solutes.

For this, a stock solution was prepared that contains the active principle in a mixture of solvents composed of ethanol, which is the best biocompatible solvent for taxane-class active principles, and of a surfactant chosen from the polysorbates sold, in particular, under the names Tween and Montanox, or the esters/ethers of ethylene oxide and of fatty acid glycerides (hydrogenated or non-hydrogenated castor oil) sold, for example, under the name Cremophor or Emulphor.

The stock solution, having a low ethanol content, preferably contains less than 5% ethanol, even more preferably it contains less than 2% ethanol. This solution is stable and may thus contain up to 200 mg/ml and preferably up to 80 mg/ml of active principle in the surfactant.

The paclitaxel stock solution had, according to that invention, a concentration between 6 and 20 mg/ml of active principle in the surfactant. The docetaxel stock solution preferably had a concentration between 20 and 80 mg/ml of active principle in the surfactant.

These solutions in the surfactant optionally contain small amounts of ethanol which may be dissolved in the perfusion solute but with extremely vigorous stirring, for example using a vortex-type apparatus.

The invention described in Patent EP 0 671 912 has made it possible to solve the problems left by the previous patent and therefore consisted in producing an intermediate solution between the solution of the taxane-class derivatives in the surfactant and an aqueous solution containing an additive that subsequently promotes the dissolution of said intermediate solution in the perfusion solute.

These additives were chosen from the set of additives that were capable of breaking up or preventing the formation of the gelled phase that is formed between the emulsifier containing the taxane-class derivative and the water.

Among the additives that make it possible to break up or prevent the formation of this gelled phase, the following were given as examples:
    ethanol;
    glucose;
    glycerol;
    propylene glycol;
    glycine;
    sorbitol;
    mannitol;
    benzyl alcohol; and
    polyethylene glycols.

The perfusions of docetaxel or of paclitaxel were then injected into a person at a flow rate that was predetermined as a function of the amount of active principle that it was desired to inject.

With all the formulations of the prior art more or less mild anaphylactic shock phenomena were observed, which had been anticipated by administration, prior to the perfusion, of an antihistamine and/or corticosteroid.

Among the recent solutions that have made it possible to prevent the appearance of these anaphylactic manifestations, formulations have appeared where the taxoid is encapsulated in an albumin-based envelope. This solution prevents the appearance of anaphylactic shocks and therefore avoids the pre-treatment with antihistamines and/or corticosteroids and allows the administration of stronger doses with reduced side effects relative to the solutions of the prior art. This formulation is, for example, described in U.S. Pat. No. 6,537,579.

Patent Application US 2003/0099674 claims lyophilised compositions composed of a taxoid dissolved in an oil droplet that is encapsulated by a surfactant. This lyophilised formulation does not collapse and does not degrade during storage. The oil described contains medium-chain triglycerides (Miglyol 812N or MCT) and soybean oil, amongst many other oils. It is written on page 7 [0072] that these lyophilisates suffer fewer losses and less deterioration than liquid emulsions. It is also mentioned [0089] that the emulsion, when it is prepared, must be subjected to lyophilisation within a matter of hours or minutes, and when it is reconstituted the lyophilisate must also be used within a matter of hours or minutes.

Among the examples, Table 2 describes solutions of paclitaxel in oil with lecithin, their stability after 36 days at 60° C. is good for Miglyol and soybean oil. A solution containing water with sesame oil is also described.

Among the emulsions obtained by dissolving the lyophilisate, only stabilities carried out at −20° C. over 1 month are described. These stability conditions do not exhibit any advantage compared to the solutions described in the first patents with regard to their stability, our objective being to obtain ready-to-use formulations that are stable over at least one year at ambient temperature.

To date, formulations are always being sought that make it possible to administer sufficient doses of taxoid-class agents while avoiding using surfactants of the polyoxyethylenated castor oil or polysorbate type, and in which the taxoid is stable at ambient temperature and is in a liquid form that can be mixed with the perfusion solute without the appearance of physical phenomena that result in phase separation, that is to say either the precipitation or the separation of liquid phases. In addition, formulations are sought that make it possible to administer the taxoid as a bolus while avoiding perfusions.

In addition, the desired formulation must allow the product to be kept stable at ambient temperature over time and must prevent the degradation of the taxoid, for example via hydrolysis.

The present invention responds to these objectives and relates to an emulsion, based on a pharmaceutically acceptable oil in water in the presence of lecithin or a semi-synthetic phospholipid, and containing the taxoid.

Among the pharmaceutically acceptable oils, mention may be made of soybean oil used alone or of medium-chain (C8-C10) triglycerides such as Miglyol™ or MCT™ used alone, or else preferably it is possible to use a mixture of soybean oil and MCT. In particular, the weight ratio of the soybean oil to the triglyceride is 1:1.

The emulsion is formed by the addition of soybean or egg lecithin, preferably egg lecithin such as that sold under the trademark Lipoid E80, or by preferential addition of a phosphatidylcholine, which is a zwitterionic surfactant.

The emulsion has a better physical stability when the lecithin or the phosphatidylcholine is combined with an anionic phospholipid chosen, in particular, from phosphatidylglycerols or phosphatidic acids.

Among the phosphatidylglycerols, mention may be made of dilauroylphosphatidylglycerol (DLPG), di-myristoyl-phosphatidylglycerol (DMPG) or dipalmitoylphosphatidylglycerol (DPPG). Among the phosphatidic acids, mention may be made of the sodium salts of dilauroylglycerophosphatidic acid (DLPA), of dimyristoylglycerophosphatidic acid (DMPA) or of dipalmitoylglycerophosphatidic acid (DPPA).

The weight ratio of, respectively, the lecithin or of the phosphatidylcholine to the phosphatidylglycerol or to the phosphatidic acid is preferably between 500 and 3 and more preferably still between 100 and 10. Among all the anionic phospholipids, dilauroylphosphatidylglycerol is preferred.

The pH of the formulation may be adjusted between 3 and 7 by addition of acid. Preferably a buffer is used to keep the pH in this region, possibly in combination with an acid. The buffer is preferably histidine. It is preferred to use 5 mM to 50 mM of histidine in the solution. The acid is preferably chosen from hydrochloric acid, citric acid or ascorbic acid.

The isotonicity of the solution may be adjusted by addition of glycerol.

It is possible to use 0 to 2% ethanol for ease of preparing the formulation.

Preferably, the weight composition of the formulation is within the following limits:

| | |
|---|---|
| oily phase | 10 to 30% |
| lecithin or phosphatidylcholine | 0.6 to 5% |
| phosphatidylglycerol | 0.01 to 0.2% |
| glycerol | 0 to 2.5% |
| ethanol | 0 to 2% |
| water | qs for 100% |

The preparation of the emulsion is preferably carried out using a microfluidization apparatus or a high-pressure homogenizer so as to obtain droplets having a size between 100 nm and 1 μm and preferably between 100 and 500 nm. Formulations where the average size of the droplets is between 150 and 350 nm are even more particularly preferred. The final formulation is inerted, preferably by nitrogen or by an inert gas that does not contain oxygen.

The concentrations of active principle of formula (I) or of formula (II) are less than 10 mg/ml and are especially used at a concentration between 0.5 and 6 mg/ml and preferably around 4 mg/ml.

The invention will be described more fully with the aid of the following examples, which should not be considered as limiting the invention.

EXAMPLE 1

1 g of DPPC and 0.03 g of DLPG were dissolved at 60° C. in a mixture of MCT (10 g), soybean oil (10 g) and ethanol (0.4 g).

0.4 g of the compound of formula (I) was dissolved in lipid solution obtained previously.

2.5 g of glycerol were added, with stirring, to 75.7 g of a 10 mM aqueous histidine buffer until a homogeneous mixture was obtained.

The aqueous phase was added to the oily phase and the whole mixture was homogenized in a mill (Ultra-Turrax) before passing into a Microfluidizer (11 cycles at 11 000 psi). The size of the droplets obtained was around 250 nm.

EXAMPLE 2

1 g of DPPC and 0.03 g of DLPG were dissolved at 60° C. in a mixture of MCT (10 g), soybean oil (10 g) and ethanol (2 g).

0.4 g of the compound of formula (I) was dissolved in lipid solution obtained previously.

2.5 g of glycerol were added, with stirring, to 75.7 g of a 10 mM aqueous histidine buffer adjusted to pH 6 (HCl) until a homogeneous mixture was obtained.

The aqueous phase was added to the oily phase and the whole mixture was homogenized in the Ultra-Turrax before passing into a Microfluidizer (11 cycles at 11 000 psi). The size of the droplets obtained was around 280 nm.

EXAMPLE 3

1.2 g of Lipoid E80 and 0.03 g of DLPG were dissolved at 60° C. in a mixture of MCT (10 g) and soybean oil (10 g).

0.4 g of the compound of formula (I XRP9881) was dissolved in lipid solution obtained previously.

2.5 g of glycerol were added, with stirring, to 75.7 g of a 10 mM aqueous histidine buffer until a homogeneous mixture was obtained.

The aqueous phase was added to the oily phase and the whole mixture was homogenized in the Ultra-Turrax before passing into a Microfluidizer (11 cycles at 11 000 psi). The average size of the droplets obtained was around 140 nm ($Dv_{50}$).

Physical stability after 1 month at 60° C.: sizes unchanged ($Dv_{50}$ and $Dv_{90}$).

EXAMPLE 4

1.2 g of Lipoid E80 and 0.03 g of DLPG were dissolved at 60° C. in a mixture of MCT (10 g) and soybean oil (10 g).

0.4 g of the compound of formula (I XRP9881) was dissolved in lipid solution obtained previously.

2.5 g of glycerol were added, with stirring, to 75.7 g of a 10 mM aqueous histidine buffer adjusted to pH 6 (HCl) until a homogeneous mixture was obtained.

The aqueous phase was added to the oily phase and the whole mixture was homogenized in the Ultra-Turrax before passing into a Microfluidizer (11 cycles at 11 000 psi). The average size of the droplets obtained was around 140 nm ($Dv_{50}$).

Physical stability after 1 month at 60° C.: sizes unchanged ($Dv_{50}$ and $Dv_{90}$).

EXAMPLE 5

1 g of DPPC and 0.03 g of DLPG were dissolved at 60° C. in a mixture of MCT (10 g), soybean oil (10 g) and ethanol (0.4 g).

0.4 g of the compound of formula (I XRP9881) was dissolved in lipid solution obtained previously.

2.5 g of glycerol were added, with stirring, to 75.7 g of a 10 mM aqueous histidine buffer adjusted to pH 6 (HCl) until a homogeneous mixture was obtained.

The aqueous phase was added to the oily phase and the whole mixture was homogenized in the Ultra-Turrax before passing into a Microfluidizer (11 cycles at 11 000 psi).

The average size of the droplets obtained was around 280 nm ($Dv_{50}$).

Physical stability after 1 month at 60° C.: sizes unchanged ($Dv_{50}$ and $Dv_{90}$).

EXAMPLE 6

1.2 g of Lipoid E80 and 0.03 g of DMPG were dissolved at 60° C. in a mixture of MCT (10 g) and soybean oil (10 g).

0.4 g of the compound of formula (I XRP9881) was dissolved in lipid solution obtained previously.

2.5 g of glycerol were added, with stirring, to 75.7 g of WFI water until a homogeneous mixture was obtained.

The aqueous phase was added to the oily phase and the whole mixture was homogenized in the Ultra-Turrax before passing into a Microfluidizer (11 cycles at 11 000 psi). The average size of the droplets obtained was around 140 nm ($Dv_{50}$).

Physical stability after 1 month at 60° C.: sizes unchanged ($Dv_{50}$ and $Dv_{90}$).

EXAMPLE 7

1.2 g Lipoid E80 and 0.03 g of DPPA were dissolved at 60° C. in a mixture of MCT (10 g) and soybean oil (10 g).

0.4 g of the compound of formula (I XRP9881) was dissolved in lipid solution obtained previously.

2.5 g of glycerol were added, with stirring, to 75.7 g of WFI water until a homogeneous mixture was obtained.

The aqueous phase was added to the oily phase and the whole mixture was homogenized in the Ultra-Turrax before passing into a Microfluidizer (11 cycles at 11 000 psi). The average size of the droplets obtained was around 140 nm ($Dv_{50}$).

Physical stability after 1 month at 60° C.: sizes unchanged ($Dv_{50}$ and $Dv_{90}$).

EXAMPLE 8

1 g of DPPC and 0.03 g of DLPG were dissolved at 60° C. in a mixture of MCT (10 g), soybean oil (10 g) and ethanol (0.4 g).

0.4 g of the compound of formula (II XRP6258) was dissolved in lipid solution obtained previously.

2.5 g of glycerol were added, with stirring, to 75.7 g of a 10 mM aqueous histidine buffer adjusted to pH 6 (HCl) until a homogeneous mixture was obtained.

The aqueous phase was added to the oily phase and the whole mixture was homogenized in the Ultra-Turrax before passing into a Microfluidizer (11 cycles at 11 000 psi).

The average size of the droplets obtained was around 260 nm.

COMPARATIVE EXAMPLE

The following example was carried out in comparison with Patent Application US 2003/0099674 to show that lyophilisation is a technology that cannot be applied to the formulations of the invention because it gives rise to an enlargement of the lipid particles of the invention.

1. Materials and Methods 1.1. Materials

Lipoid E80—batch 1031471-7/906: supplier: LIPOID KG.

Miglyol 812

Maltose monohydrate.

Saccharose.

1.2. Formula

| Formula | % | Unit (g) | |
|---|---|---|---|
| XRP9881* | 0.340 | 0.002 | 0.007 |
| Miglyol 812 | 17.0 | 0.085 | 0.340 |
| Lipoid E80 | 1.0 | 0.005 | 0.020 |

| Formula | % | Unit (g) | |
| --- | --- | --- | --- |
| Purified water | 66.6 | 0.333 | 1.333 |
| Cryoprotectant | 15.0 | 0.075 | 0.300 |
| Total | 100 | 0.5 | 2 |
| Lyophilisate height | | 1 mm | 6 mm |

*pure, solvent-free product 1.3. Emulsion Preparation Method
1) Dissolution of the active principle in the oil.
2) Pre-dispersion of the oily phase in water+lecithin using the Ultra-Turrax.
3) Homogenization through a microfluidizer at 11 000 psi (11 passes).
4) Division of the emulsion into 2 fractions—Addition of 15% maltose or saccharose.
5) Spreading qs for a height of 1 mm and 6 mm.
6) Lyophilisation: The conditions applied are described below. Freezing: shelf temperature −45° C.—product temperature −39° C.
Sublimation: shelf temperature −25° C.—pressure 50 microbar.
Secondary drying at 30° C.
2. Results
2.1. Before Lyophilisation
Size before addition of cryoprotectants 250 nm (Coulter N4+, measurement method: quasi-elastic light scattering).
No change in the size after addition of cryoprotectants (before lyophilisation).
2.2. After Lyophilisation
2.2.1. Appearance and Reconstitution
Appearance of the lyophilisate: no collapse or shrinkage→correct appearance.
Reconstitution with WFI water: immediate reconstitution, the emulsion obtained is of homogeneous appearance.
2.2.2. Size after Reconstitution
Presence of vesicles having a size between 300 nm and 10 μm (metastable system).
No visible or measured difference between maltose and saccharose, nor between lyophilisate heights of 1 and 6 mm.

What is claimed is:

1. A composition that can be injected in the form of an emulsion containing a derivative of the taxane class, comprising an emulsion based on a pharmaceutically acceptable oil in water and on lecithin, wherein the taxane is dissolved and corresponds to formula (II) below:

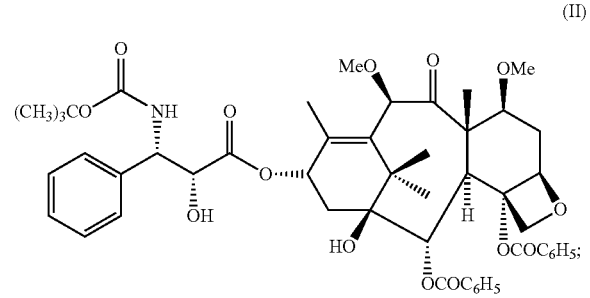

(II)

and wherein the composition also comprises an anionic surfactant.

2. The composition according to claim 1, wherein the pharmaceutically acceptable oil is chosen from mixtures of soybean oil and of medium-chain triglycerides.

3. The composition according to claim 1, wherein the lecithin is a natural lecithin chosen from egg lecithin or soy lecithin or a semi-synthetic lecithin chosen from phosphatidylcholines.

4. The composition according to claim 1, wherein the anionic surfactant is a phosphatidylglycerol or a phosphatidic acid.

5. The composition according to claim 4, wherein the phosphatidylglycerol is chosen from the group consisting of dilauroylphosphatidylglycerol (DLPG), dimyristoylphosphatidylglycerol (DMPG) and dipalmitoylphosphatidyl-glycerol (DPPG).

6. The composition according to claim 4, wherein the phosphatidic acid is chosen from the sodium salts dilauroylglycerophosphatidic acid (DLPA), of dimyristoylglycerophosphatidic acid (DMPA) and of dipalmitoylglycerophosphatidic acid (DPPA).

7. The composition according to claim 4, wherein the weight ratio of lecithin to the phosphatidylglycerol or to the phosphatidic acid is between 500 and 3.

8. The composition according to claim 7, wherein the weight ratio is between 100 and 10.

9. The composition according to claim 1, wherein the pH of the formulation is adjusted to between 3 and 7 by addition of acid.

10. The composition according to claim 9, wherein the acid is chosen from hydrochloric acid, citric acid and ascorbic acid.

11. The composition according to claim 1, further comprising a histidine buffer.

12. The composition according to claim 1, wherein the isotonicity of the solution is adjusted by addition of glycerol.

13. The composition according to claim 1, wherein the weight composition of the formulation is within the following limits:

| | |
| --- | --- |
| oily phase | 10 to 30% |
| lecithin or phosphatidylcholine | 0.6 to 5% |
| phosphatidylglycerol | 0.01 to 0.2% |
| glycerol | 0 to 2.5% |
| ethanol | 0 to 2% |
| water | qs for 100%. |

14. The composition according to claim 1, which is administered intravenously as a bolus.

15. The composition according to claim 1, wherein the particles have a size between 100 nm and 1 μm.

16. A method of preparing the composition according to claim 1, comprising producing the emulsion using a microfluidization apparatus or a high-pressure homogenizer.

17. A composition that can be injected in the form of an emulsion containing a derivative of the taxane class, comprising an emulsion based on a pharmaceutically acceptable oil in water and on lecithin, wherein the taxane is dissolved and corresponds to formula (II) below:

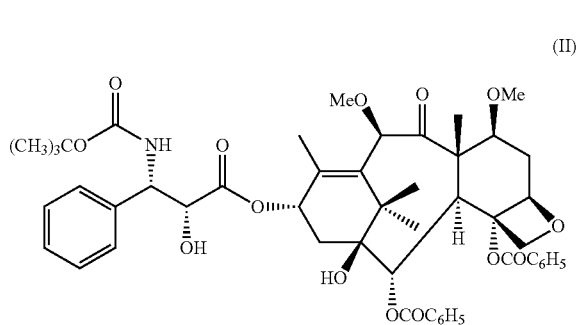

and wherein the composition also comprises an anionic surfactant.

18. The composition according to claim 17, wherein the pharmaceutically acceptable oil is chosen from mixtures of soybean oil and of medium-chain triglycerides.

19. The composition according to claim 17, wherein the anionic surfactant is a phosphatidylglycerol or a phosphatidic acid.

20. A composition that can be injected in the form of an emulsion containing a derivative of the taxane class, comprising an emulsion based on a pharmaceutically acceptable oil in water and on lecithin, wherein the taxane is dissolved and corresponds to formula (II) below:

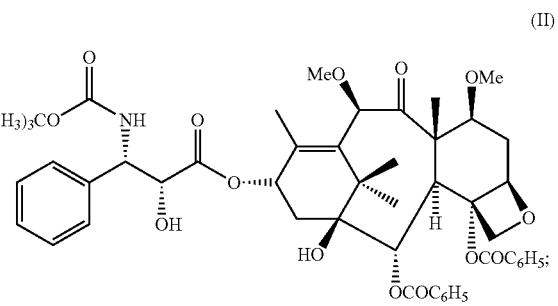

wherein the composition also comprises an anionic surfactant which is a phosphatidylglycerol or a phosphatidic acid and wherein the pharmaceutically acceptable oil is chosen from mixtures of soybean oil and of medium-chain triglycerides.

* * * * *

UNITED STATES PATENT AND TRADEMARK OFFICE
CERTIFICATE OF CORRECTION

PATENT NO. : 8,481,589 B2  
APPLICATION NO. : 12/757255  
DATED : July 9, 2013  
INVENTOR(S) : Patricia Rortais and Carine Gachon It is certified that error appears in the above-identified patent and that said Letters Patent is hereby corrected as shown below:

In the Specification and Claims,

In Column 1, lines 24-26; Column 7, lines 51-65; Column 9, lines 1-14; and Column 10, lines 5-18, for each occurrence, please delete the figure referred to as formula (II) and insert the following figure:

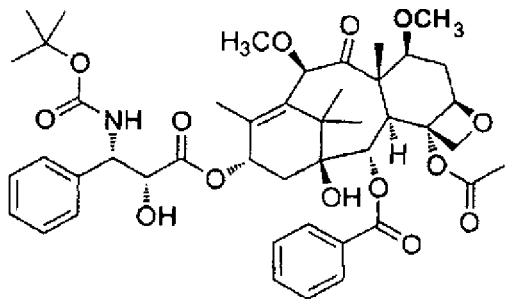

-- --

Signed and Sealed this  
Eighteenth Day of August, 2015

Michelle K. Lee  
*Director of the United States Patent and Trademark Office*